US011330974B2

(12) United States Patent
Kaya

(10) Patent No.: US 11,330,974 B2
(45) Date of Patent: May 17, 2022

(54) ENDOMICROSCOPIC DEVICE

(71) Applicant: Yeditepe Universitesi, Istanbul (TR)

(72) Inventor: Ahmet Hilmi Kaya, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 376 days.

(21) Appl. No.: 16/340,154

(22) PCT Filed: Jun. 23, 2017

(86) PCT No.: PCT/TR2017/050289
§ 371 (c)(1),
(2) Date: Apr. 8, 2019

(87) PCT Pub. No.: WO2018/067082
PCT Pub. Date: Apr. 12, 2018

(65) Prior Publication Data

US 2019/0223709 A1 Jul. 25, 2019

(30) Foreign Application Priority Data

Oct. 7, 2016 (TR) ................................ 2016/14129

(51) Int. Cl.
*A61B 1/313* (2006.01)
*A61B 1/00* (2006.01)
(Continued)

(52) U.S. Cl.
CPC .............. *A61B 1/313* (2013.01); *A61B 1/005* (2013.01); *A61B 1/00147* (2013.01);
(Continued)

(58) Field of Classification Search
CPC . A61B 1/00147; A61B 1/00195; A61B 1/005; A61B 1/0669; A61B 1/313; A61B 1/00188
See application file for complete search history.

(56) References Cited

U.S. PATENT DOCUMENTS 5,095,887 A 3/1992 Leon
5,601,549 A * 2/1997 Miyagi .............. A61B 1/00193 606/4

(Continued)

FOREIGN PATENT DOCUMENTS

CN 103892916 A 7/2014
JP H08131455 A 5/1996

(Continued)

*Primary Examiner* — Aaron B Fairchild
(74) *Attorney, Agent, or Firm* — Bayramoglu Law Offices LLC

(57) ABSTRACT

An endomicroscopic device, which, in microsurgical operations, enables the deep surgical sites that cannot be seen from a certain angle to become visible. The endomicroscopic device includes a light source to illuminate the surgical site, a microscope lens for taking and magnifying an image of a tissue at the surgical site, a pair of binocular eyepieces for projecting the image to eyes of the surgeon, an endoscopic probe for displaying blind areas outside of a field of view of the at least one microscope lens from different angles in a periscopic manner, an endoscopic probe outlet, and a distal portion located at an end of the endoscopic probe. The distal portion is flexible and can be angled to be directed to different areas, and provides a second periscopic image.

2 Claims, 1 Drawing Sheet

1
4
6
3
5
2
7

(51) Int. Cl.

| | |
|---|---|
| ***A61B 1/005*** | (2006.01) |
| ***A61B 1/06*** | (2006.01) |
| ***A61B 90/20*** | (2016.01) |
| ***G02B 23/24*** | (2006.01) |
| ***A61B 5/00*** | (2006.01) |
| *A61B 90/00* | (2016.01) |

(52) U.S. Cl.

CPC ........ *A61B 1/00195* (2013.01); *A61B 1/0669* (2013.01); *A61B 5/4064* (2013.01); *A61B 90/20* (2016.02); *G02B 23/2423* (2013.01); *A61B 90/361* (2016.02); *A61B 2505/05* (2013.01)

(56) References Cited

U.S. PATENT DOCUMENTS

| | | | | |
|---|---|---|---|---|
| 5,742,429 | A * | 4/1998 | Tsumanuma ....... | A61B 1/00193 359/377 |
| 6,088,154 | A | 7/2000 | Morita | |
| 6,398,721 | B1 | 6/2002 | Nakamura et al. | |

FOREIGN PATENT DOCUMENTS

| | | | |
|---|---|---|---|
| JP | 2001198140 | A | 7/2001 |
| JP | 2003070716 | A | 3/2003 |

* cited by examiner

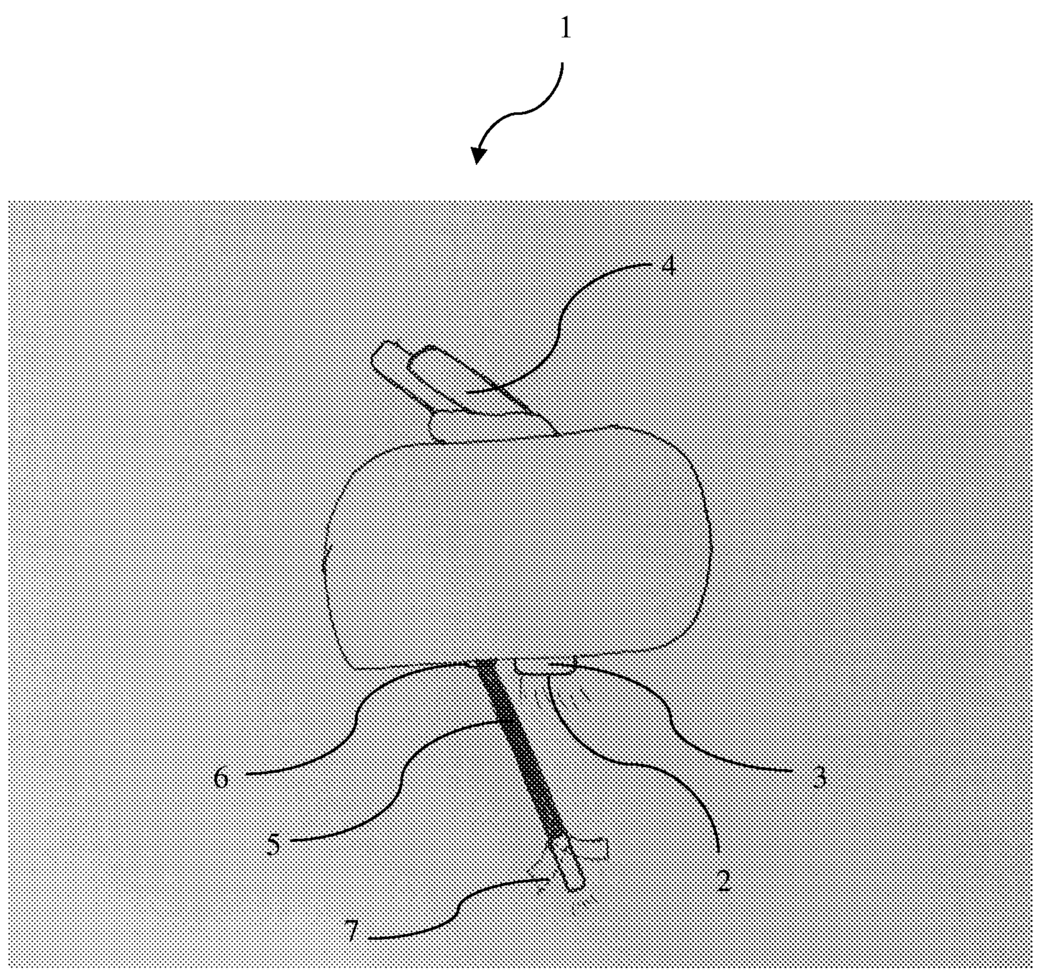
1
4
6
3
5
2
7

ENDOMICROSCOPIC DEVICE

CROSS REFERENCE TO THE RELATED APPLICATION

This application is the national phase entry of International Application No. PCT/TR2017/050289, filed on Jun. 23, 2017, which is based on and claims priority to the Turkish Patent Application No. 2016/14129, filed on Oct. 7, 2016, the entire contents of which are incorporated herein by reference.

TECHNICAL FIELD

The present invention relates to an endomicroscopic device which is used for viewing deep surgical sites that are difficult to reach in microsurgical operations.

BACKGROUND

Today, microsurgical operations employed in neurosurgery depend on certain standards. These operations can be summarized as follows:

In microsurgery, a device called microscope is provided between the site to be operated and the surgeon. A light source and a lens system are provided at the part of the microscope facing the surgical site and a binocular eyepiece at the part thereof facing the surgeon. That is to say, the microscope, by the help of a lens, takes and magnifies the image of the tissue at the surgical site illuminated by the light source and projects the image to the eyes of the surgeon via the binocular eyepieces. Thus, the surgeon sees the tissue more clearly and in magnified view compared to naked eye. The surgeon intervenes with the tissue under the said image via millimetric tools called microsurgical instruments that s/he holds, i.e. performs the surgery.

In brain surgeries performed by microsurgery, usually natural pathways such as clefts or fissures are used as the entrance point for reaching the areas at the depths of the brain. For example, the sulcus called Sylvian fissure is located between the frontal lobe and temporal lobe. This sulcus is circumscribed deeply by the arachnoid membrane which is one of the layers of meninges. The surgeon views this sulcus clearly and in a magnified manner under the microscope and half-opens this membrane with the micro instruments and goes deeper through this sulcus. This way, the surgeon reaches many sites at the depths without having to cut the brain tissue. The sites reached through this cleft are frontal and temporal lobe inner surfaces, insular lobe, main veins supplying the brain (middle cerebral artery, carotid artery, anterior cerebral artery and branches), both optic nerves, pituitary gland region and above. The surgeon reaches such sites through the said cleft or similar natural pathways and if there is a tumor, removes the tumor again under the microscope without affecting the surrounding tissue. If there is an aneurysm in the vein, the surgeon places a clip to occlude the neck of the aneurysm and finally performs the necessary operations on the said sites. The most restricting factor when performing these operations under the microscope iss as follows: When the surgeon is performing these operations, s/he can only see the parts in the visibility range of the microscope and thus cannot see the recesses outside of the visibility range. S/he tries to include the recesses outside of the visibility range into the field of view of the microscope by excluding (pulling) the surface area, and thus to see the recesses. However the surgeon cannot include the sites that require pulling the tissue more than it can tolerate into the field of view. Since these sites will remain as blind areas during the surgery, the surgeon cannot intervene with these sites.

In the recent years, endoscopic systems are also used in neurosurgery. Endoscopic systems provide additional advantages. For example, if an endoscopic probe is inserted to the surgery site, wherein the surgeon goes deep during the surgery, the recesses in the deep regions and the blind spots outside of the field of view of the microscope become visible. Furthermore, while the endoscopic probe enables to view the recesses, which cannot be viewed by the microscope, it also enables to view this deep region from different angles. However there are several reasons restricting use of endoscopic surgery. These reasons are described below:

Since some of the endoscopic devices are designed such that the camera tip and the other surgical instruments are passed through a single carrier port, the surgical instruments cannot be used comfortably in a wide movement range as the microsurgical instruments, because introducing all these instruments through a single tubular port hinders movements of a wider angle. It is not possible to dissect along the brain sulcus and reach the depths of the brain through a single carrier port. The depths can be reached by inserting this port into the brain tissue and this situation causes to reach the points, which normally can be accessed through natural pathways without cutting or drilling the brain tissue, by passing through the brain tissue.

If the surgeon continues with the surgery with an endoscopic probe, which s/he manipulates by hand and inserts to the depths, instead of a single carrier tube; since s/he can hold the surgical instrument only with her/his other hand, s/he will be dependent on a single surgical instrument and her/his manipulation ability will be reduced. For example, the surgeon cannot practically perform basic operations such as half opening and also burning the tissue, stretching the tissue and cutting the membrane bands in between and aspiration which are all performed by two hands. This also increases the risk of injuring the tissue as it causes inadequacy during the surgical operation. Sometimes, in order to overcome this problem, the endoscopic probe is inserted into the surgical site by a second surgeon assisting the surgery and the surgery is performed by the first surgeon by two hands under the image obtained this way. This requires two surgeons to work simultaneously in the narrow area of brain surgery and causes extreme technical difficulties. This process also leads to problems in terms of comfort and safety.

Furthermore, whether the endoscopic system used via a single carrier system or as a free probe, when it is inserted to the depths; since it is not connected to a fixed system, the wide movement behind the end part may cause injury (tissue tear, vein rupture) due to tension on the brain surface area where it is inserted, and thus safe control thereof is difficult. Therefore today, endoscopic systems can be used with due safety in brain surgeries in a modern manner in the head base region accessed by entering through the nose, or in spinal surgeries accessed by entering through the soft tissue, because in these sites, since, when the system is moved from the entrance point to the site it reaches, the stretched tissue is only the tissue such as nasal cavity and walls and the muscle and soft tissues around the spinal cord, stretching does not cause any tissue injuries at these sites and it can be used at these sites with wide-angle movements.

Thus to sum up:

In brain surgeries, the microscope enables the surgeon to work comfortably by two hands. Furthermore, it presents a wide range of microsurgical instruments (bone cutting tools, aspirating tools, burning bipolar tools, arachnoid membrane openers called hooks, microscissors, dissectors, aspirators, etc.) which have been produced for years. All of these instruments can be optimally oriented to different angles with two hands by hand and wrist rotation.

In addition, by means of endoscopic surgery, the areas where the microscope is blind can be seen in detail and from different angles. However, due to the above mentioned restricting factors, it cannot be used safely and comfortably, and there is no opportunity of a rich range of instruments such as classical microsurgical instrument portfolio in endoscopic systems working via a single port. When the endoscopic probe is inserted by hand, the surgeon lacks the comfort and safety of ability to work by two hands.

Thanks to the present invention, a new device is developed which enables to overcome the problems in the art and enables the surgeon to use it with the same comfort and in an effortless and safe manner.

SUMMARY

The objective of the present invention is to provide an endomicroscopic device, which, in microsurgical operations, enables the deep surgical regions that cannot be seen from a certain angle to become visible.

Another objective of the present invention is to provide an endomicroscopic device, which enables the surgeon to perform operations with two hands by using the microsurgery instruments.

A further objective of the present invention is to provide an endomicroscopic device which provides a second periscopic image during surgery.

BRIEF DESCRIPTION OF THE DRAWINGS

The "endomicroscopic device" developed to fulfill the objectives of the present invention is illustrated in the accompanying FIGURE, in which:

FIG. 1 is the view of the endomicroscopic device of the present invention.

The components shown in the figures are each given reference numbers as follows:

1. Endomicroscopic device
2. Light source
3. Microscope lens
4. Binocular eyepiece
5. Endoscopic probe
6. Endoscopic probe outlet
7. Distal portion

DETAILED DESCRIPTION OF THE EMBODIMENTS

The endomicroscopic device (1) of the present invention essentially comprises

- at least one light source (2) which is located at the part facing the surgical site and which enables to illuminate the surgical site,
- at least one microscope lens (3) which takes and magnifies the image of the tissue at the surgical site,
- a pair of binocular eyepieces (4) that projects the taken image to the eyes of the surgeon,
- at least one endoscopic probe (5) which is movable and can display the blind areas that are outside of the field of view of the microscope lens (3) from different angles in a periscopic manner,
- at least one endoscopic probe outlet (6),
- at least one distal portion (7), which is located at the end of the endoscopic probe (5), and which is flexible and can be angled to be directed to different areas, and provides a second periscopic image.

The endomicroscopic device (1) of the present invention is used in order to view the recesses in the deep brain tissue from different angles in brain surgeries performed by microsurgery.

By means of the device of the present invention, the surgeon will be able to practically reach the deep brain tissue, and upon continuing with the surgery, s/he will be able to insert the periscopic endoscopic probe, which comes out of the microscope base with a single button under the microscopic lens image, along the trace through which it passes to the surgery site. When the surgeon inserts the periscopic endoscopic probe to the depths under the lens image, s/he will be able to switch to endoscopic view again by a single button and perform operation on the blind areas, which are not covered by the microscope, with two hands under this view by using the desired microsurgical instruments. The flexible movement ability that can be provided to the periscopic endoscopic probe will provide the opportunity of viewing the recesses from different angles upon being operated via a single button.

The surgeon will be able switch between the microscope lens image and periscopic endoscopic probe image via a single button or a multiple function button. Such a device will carry the surgical operations performed in neurosurgery one step forward. For example, a surgeon who reaches the $3^{rd}$ ventricle anterior by microsurgery via anterior interhemispheric route will be able to access the $3^{rd}$ ventricle posterior as well by means of the periscopic probe; or a surgeon, who reaches cerebellopontine cisterna via retrosigmoid approach, will be able to access lateral and anterior brainstem (pons, medulla oblongata) when s/he inserts the periscopic probe.

By means of the present invention, additional possibilities will come to the fore for approaching the anatomic area in brain surgery, and the morbidity and mortality risks of the patient will be directly reduced by many advantages such as removal of a larger part of the lesion more safely, and visibility of an anatomic area which could not be viewed from a certain angle. Thus, operability success of the patient will increase directly.

The device of the present invention will be able to be used at classical endoscopic head base and also in spinal surgery, and can be an alternative to the endoscopic surgery used currently at these sites with more different advantages.

The endomicroscopic device of the present invention is also an extremely suitable device for robotic surgery whose use in neurosurgery and spinal surgery may be brought to the agenda. If the same device is used with the multiple (more than 2) robotic arms controlled by the surgeon, it will perform all the operations that will be performed by the surgeon bimanually, and will also provide an opportunity of safer and more practical use. Thus, this device is also a suitable device that can be devised for a robotic system.

As a conclusion, this device enables both to apply the current surgical methods which have been experienced for years, and to use the surgical instruments portfolio, which has been produced from the past to present. It is also advantageous in terms of cost; and it is a device which provides serious technical solutions and gives way to innovations in neurosurgery. It is an assertive device which can also be used in robotic neurosurgery.

Even though a technical drawing has been provided for the endomicroscopic model, the device can be modified maintaining the basic principle. The important point in the present invention is that, under a system such as a microscope, which transfers image outside of the tissue, there is provided a second periscopic display system taking images from the depths of the tissue, and that the two systems support each other in practice. Modifications can be made maintaining the basic logic of the invention.

What is claimed is:

1. An endomicroscopic device, comprising:

a microscope having a bottom side and an outlet in the bottom side, at least one microscope lens for taking and magnifying an image of a surgical site from the bottom side, a pair of binocular eyepieces for projecting the image to eyes of a surgeon, at least one light source located with the lens to illuminate the surgical site, at least one periscopic display system integrated with the microscope, the periscopic display system configured to selectively display to the surgeon by way of the eyepieces an endoscopic image of blind areas outside of a field of view of the at least one microscope lens from different angles in a periscopic manner, the periscopic display system has a button-actuated periscopic endoscopic probe having a flexible terminal end configured for controlled movement, including bending at an angle, out of an outlet formed in the bottom side of the microscope through a pathway to the surgery site.

2. The endomicroscopic device according to claim 1, wherein the endomicroscopic device is configured to view recesses in a deep brain tissue from different angles in brain surgeries performed by microsurgery.

* * * * *